(12) United States Patent
Edouard Naz et al.

(10) Patent No.: US 10,876,222 B2
(45) Date of Patent: Dec. 29, 2020

(54) METHODS FOR ELECTROSPIN COATING AND LAMINATING OF ENDOLUMINAL PROSTHESES

(71) Applicants: Christophe Pierre Edouard Naz, Avon (FR); Xeltis, BV, Eindhoven (NL)

(72) Inventors: Christophe Pierre Edouard Naz, Avon (FR); Anandkumar Nandakumar, The Hague (NL); Oleg Svanidze, Zurich (CH); Martijn Antonius Johannes Cox, Budel (NL); Fabio Zomer Volpato, Eindhoven (NL)

(73) Assignee: Xeltis AG, Zurich (CH)

( * ) Notice: Subject to any disclaimer, the term of this patent is extended or adjusted under 35 U.S.C. 154(b) by 58 days.

(21) Appl. No.: 15/763,197

(22) PCT Filed: Oct. 3, 2016

(86) PCT No.: PCT/IB2016/001529
§ 371 (c)(1),
(2) Date: Mar. 26, 2018

(87) PCT Pub. No.: WO2017/055926
PCT Pub. Date: Apr. 6, 2017

(65) Prior Publication Data
US 2018/0274131 A1 Sep. 27, 2018

Related U.S. Application Data

(60) Provisional application No. 62/236,073, filed on Oct. 1, 2015.

(51) Int. Cl.
*D01D 5/00* (2006.01)
*D04H 1/728* (2012.01)
(Continued)

(52) U.S. Cl.
CPC ............ *D01D 5/0084* (2013.01); *A61L 27/18* (2013.01); *A61L 27/34* (2013.01); *A61L 31/10* (2013.01);
(Continued)

(58) Field of Classification Search
CPC .. A61L 33/00; A61F 2/06; C08K 5/06; D01D 5/0084; D01D 5/0061
See application file for complete search history.

(56) References Cited

U.S. PATENT DOCUMENTS 6,376,588 B1 * 4/2002 Nieh ...................... B29C 33/62
264/213
7,824,601 B1 * 11/2010 Stankus .................. A61L 31/14
264/131
(Continued)

FOREIGN PATENT DOCUMENTS

CN 101732117 6/2010
JP 2004532665 10/2004
(Continued)

OTHER PUBLICATIONS

Koombhongse et al., Flat Polymer Ribbons and Other Shapes by Electrospinning, 2001, Journal of Polymer Science: Part B: Polymer Physics, vol. 39 2598-2606 (Year: 2001).*
(Continued)

*Primary Examiner* — Dah-Wei D. Yuan
*Assistant Examiner* — Andrew J Bowman
(74) *Attorney, Agent, or Firm* — Lumen Patent Firm

(57) ABSTRACT

Endoluminal and other as implantable prostheses are fabricated in electrospinning apparatus including a target and an applicator. A solution comprising a polymer and a solvent is directed to the target with a first electrical potential between the target and the applicator to produce a first set of fibers. The same or another solution is continued to be delivered
(Continued)

through the applicator onto the target while applying a second electrical potential to produce a second set of fibers having a second solvent fraction, and the same or different solution may be delivered while applying a third potential difference to produce a laminated structure having at least three layers. By properly controlling the electrical potentials and solvent fractions, an adhesive layer can be formed to serve a glue or adhesive between the inner and outer layers, and a stent or other scaffold may be positioned between the inner and outer layers to form a covered stent or graft.

36 Claims, 6 Drawing Sheets

(51) Int. Cl.
    *A61L 27/34*     (2006.01)
    *A61L 31/10*     (2006.01)
    *A61L 27/18*     (2006.01)

(52) U.S. Cl.
    CPC ......... *D01D 5/0046* (2013.01); *D01D 5/0061* (2013.01); *D01D 5/0069* (2013.01); *D01D 5/0092* (2013.01); *D04H 1/728* (2013.01); *A61L 2420/02* (2013.01); *D10B 2509/06* (2013.01)

(56) References Cited

U.S. PATENT DOCUMENTS

| | | | |
|---|---|---|---|
| 2005/0137675 A1* | 6/2005 | Dubson | A61F 2/06 623/1.4 |
| 2011/0135806 A1 | 6/2011 | Grewe | |
| 2013/0268062 A1 | 10/2013 | Puckett | |
| 2014/0188212 A1 | 7/2014 | Haselby | |

FOREIGN PATENT DOCUMENTS

| | | |
|---|---|---|
| JP | 2004321484 | 11/2004 |
| WO | WO2002049535 | 6/2002 |

OTHER PUBLICATIONS

Pena, Preparation and Characterization of Electropun Poly(D,L-Lactide-Co-Glycolide) Scaffolds for Vascular Tissue Engineering and the Advancement of an In Vitro Blood Vessel Mimic, 2009, California Polytechnic University. pp. 1-163 (Year: 2009).*
Sundararaghavan et al., Gradients with Depth in Electrospun Fibrous Scaffolds for Directed Cell Behavior, 2011, Biomacromolecules, vol. 12, Issue 6, pp. 2344-2350 (Year: 2011).*

* cited by examiner

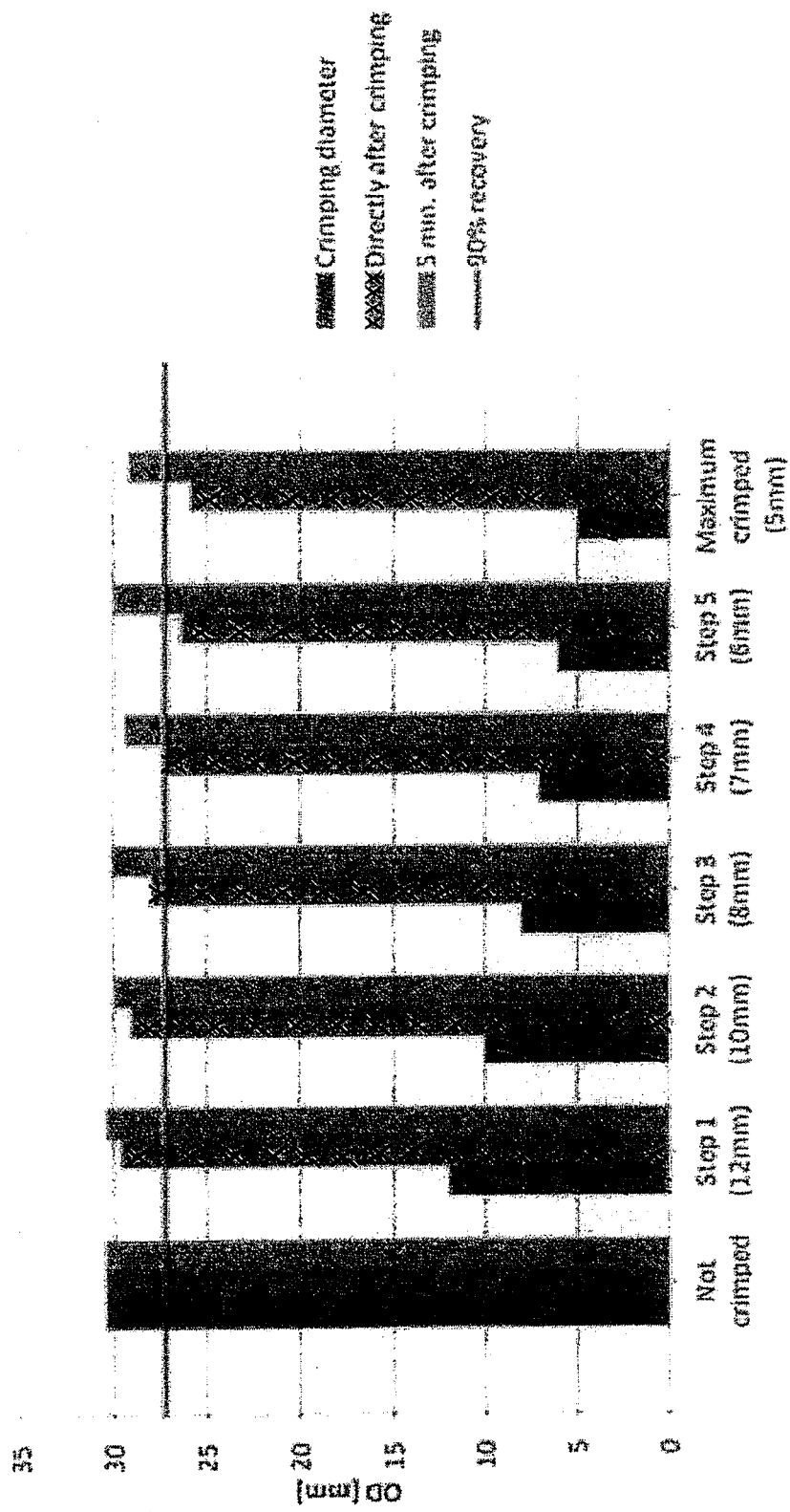
Figure 1C – OD measurements of the crimping steps

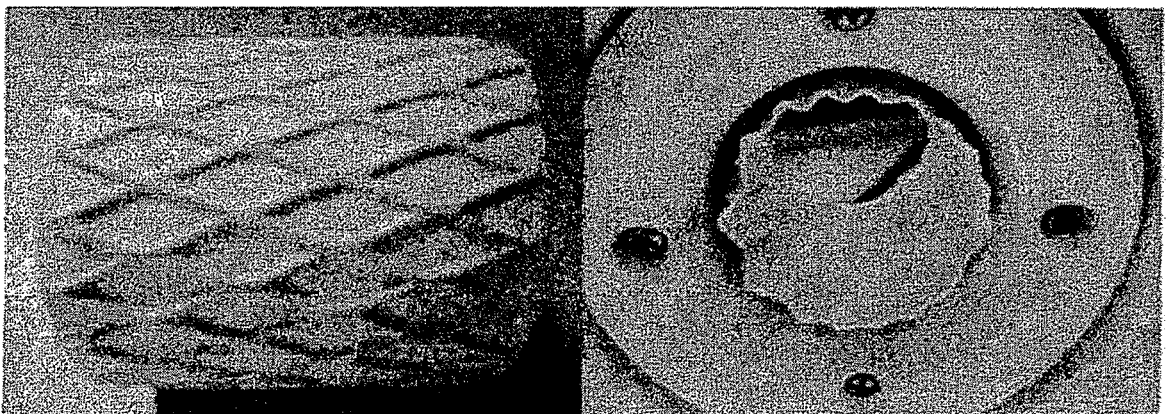
Figure 2a. before crimping; b. before start in crimping device
Figure 2c. crimped to 12mm; d. 5 minutes after crimping to 12mm
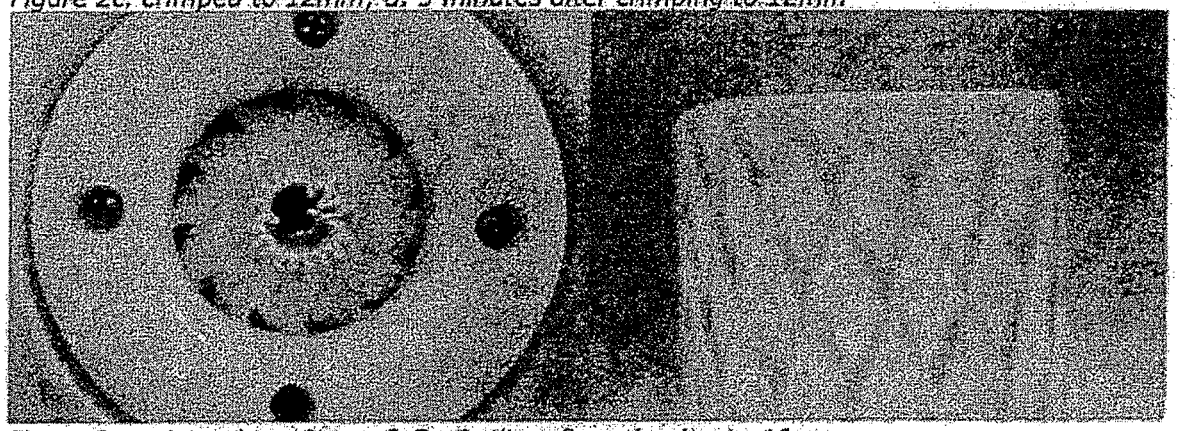
Figure 2e. crimped to 10mm; f. 5 minutes after crimping to 10mm
FIGS. 2a – 2f

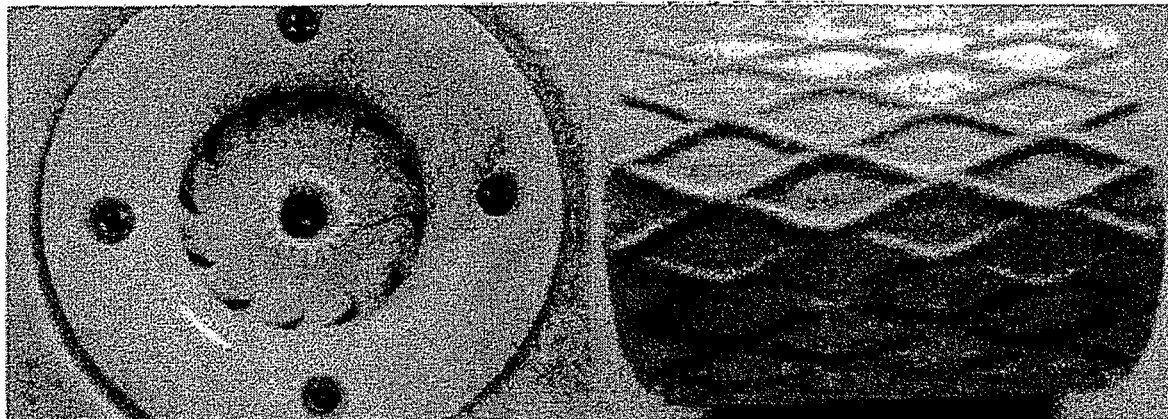
FIGS. 2g – 2l

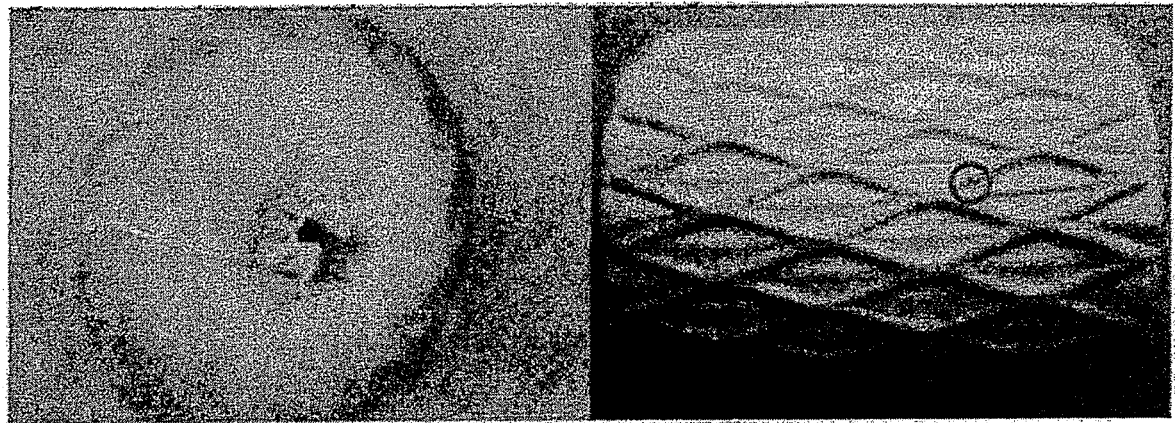
Figure 2m. crimped to 5mm; n. 5 minutes after crimping to 5mm
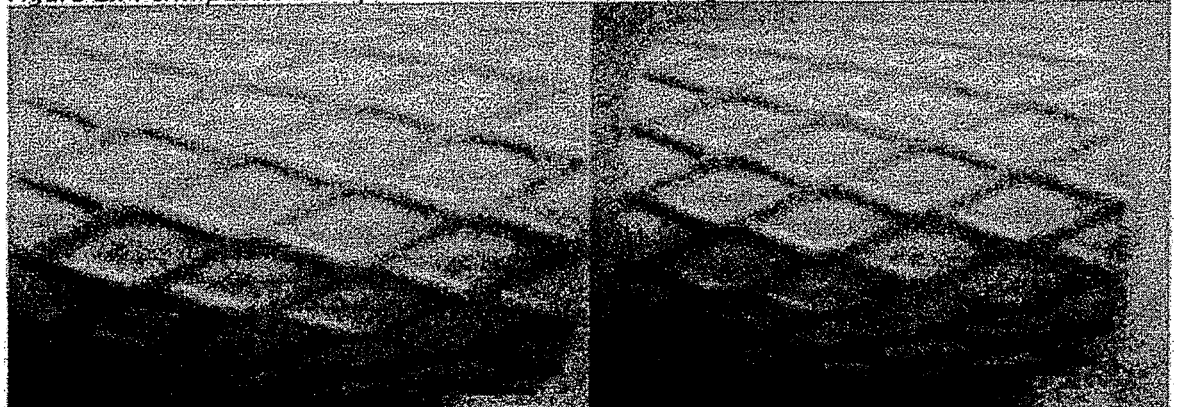
Figure 2o. t=0 wet 37°C; 2p. t=5 minutes wet 37°C
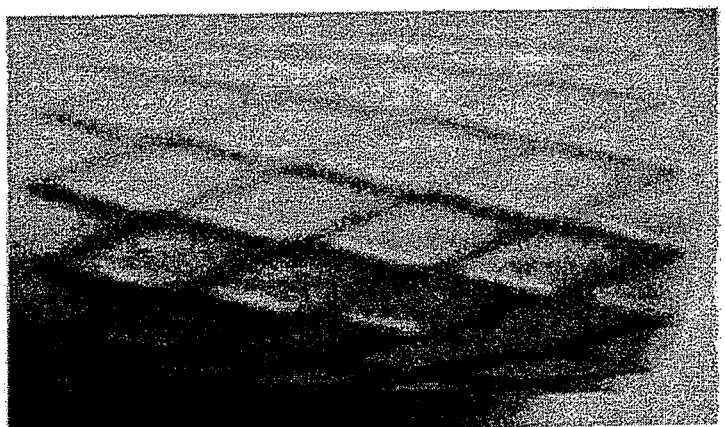
Figure 2q. t=60 minutes wet 37°C
FIGS. 2m – 2q

METHODS FOR ELECTROSPIN COATING AND LAMINATING OF ENDOLUMINAL PROSTHESES

CROSS-REFERENCE TO RELATED APPLICATIONS

This application is a 371 of PCT/IB2016/001529 filed on Oct. 3, 2016. PCT/IB2016/001529 claims the benefit of U.S. Provisional Application 62/236,073 filed on Oct. 1, 2015, the entire content of which is incorporated herein by reference.

BACKGROUND OF THE INVENTION

1. Field of the Invention

The present application relates generally to medical devices and methods. More particularly, the present invent relates to methods for coating and laminating implants such as endoluminal prostheses.

A medical stent is a type of endoluminal prosthesis which is implanted in a body lumen to open or create a passage therethrough. Most commonly, stents act as "scaffolds" to hold open a diseased or blocked region in a natural body lumen such as in the vasculature, biliary tract, and urinary tract. Stents are often coated or laminated in order to increase biocompatibility and/or create a barrier so that the stent can act as a graft. Such laminated stents or grafts are also useful for as a base or anchor for prosthetic heart and other implantable valves, as grafts for endovascular aneurysm repair (EVAR) used as treatment of thoracic and abdominal aortic aneurysms, and for other purposes Of particular interest to the present invention, US Patent Publication 2013/0238086 teaches fabrication of a stent or other prosthesis by encapsulating a scaffold or frame with a polymer coating. The polymer coating may consist of layers of electrospun polytetrafluoroethylene (PTFE). The electrospun PTFE may be porous and may permit endothelial cell growth. Such stents stent may be implanted in the central venous system, the peripheral vasculature, the abdominal aorta, the bronchioles, the esophagus, the biliary tract, or elsewhere.

While generally effective, the methods disclosed for forming these encapsulated stents require the formation of successive layers of different materials in order to "tie" the layers together. The need to apply different materials complicates the fabrication process and is therefore undesirable. Moreover, these encapsulated stents may be damaged upon crimping which in turn may limit the maximum crimping possible and the extent of recovery of the stent from crimping.

Thus, it would be beneficial to provide improved methods, materials and apparatus for laminating stents using a single material that where successive layers of the material can be fully integrated to resist delamination. It would be further desirable if the laminated stent structures could be crimped to a diameter which is less than 20% of the pre-crimped diameter, preferably less than 15% of the pre-crimped diameter, and sometimes less than 10% of the pre-crimped diameter, without significant damage to the laminated structure. It would be still further desirable if after crimping, the stents could recover to at least 90% of the pre-crimped diameter, preferably to at least 95% of the pre-crimped diameter, and sometimes to 98% or higher of the pre-crimped diameter. Stents and grafts having such improved recovery characteristics should be useful as components in transvascular and other prosthetic heart valves, as aneurysmal grafts, and for a variety of other medical uses. At least some of these objectives will be met by the inventions described hereinafter.

2. Description of the Background Art

U.S. Patent Publication 2013/0238086 has been described above. See also, U.S. Pat. No. 8,637,109 and US Patent Publ. Nos. 2013/0018220 and 2003/0211135. U.S. Pat. No. 7,922,761 describes an electrospun layer over a tubular support structure where at least one layer is impregnated with a thrombogenic material. Transcatheter valves are described in various patents and published applications, such as WO2007149933. Other references of interest include Genereux P, Head, S J, Hahn R, et al. Paravalvular Leak after Transcatheter Aortic Valve Replacement. *J Am Coll Cardiol.* 2013; 61(11):1125-1136; Kodali, S K, Williams M R, Smith C R, et al. Two-year outcomes after transcatheter or surgical aortic valve replacement. *N Engl J Med*, 2012; 366: 1686-169; McElhinney D B, Cheatham J P, Jones T K, et al. Stent Fracture, valve Dysfunction, and Right Ventricular Outflow Tract Reintervention After Transcatheter Pulmonary Valve Implantation *Circulation: Cardiovascular Interventions.* 2011; 4: 602-614; Tan J W, Yeo K K, Laird J R. Food and Drug Administration-approved endovascular repair devices for abdominal aortic aneurysms: a review. J Vasc Intery Radiol. 2008; 19 (6 Suppl): S9-S17; Matsumoto A H. What randomized controlled trials tell us about endovascular repair of abdominal aortic aneurysms. J Vasc Intery Radiol. 2008; 19 (6 Suppl): S18-21; Kranokpiraksa, P, Kaufman J A. Follow-up of endovascular aneurysm repair: plain radiography, ultrasound, CT/CT angiography, MR imaging/MR angiography, or what? J Vasc Intery Radiol. 2008; 19 (6 Suppl): S27-36; Kaufman J A, Lee M J. Vascular and interventional radiology, the requisites. Mosby Inc. (2004) ISBN: 0815143699; Rosen R J, Green R M. Endoleak management following endovascular aneurysm repair. J Vasc Intery Radiol. 2008; 19 (6 Suppl): S37-43; Kougias P, Lin P H, Dardik A et-al. Successful treatment of endotension and aneurysm sac enlargement with endovascular stent graft reinforcement. J. Vasc. Surg. 2007; 46 (1): 124-7; White S B, Stavropoulos S W. Management of Endoleaks following Endovascular Aneurysm Repair. Semin Intervent Radiol. 2009; 26 (1): 33-8; Stavropoulos S W, Charagundla S R. Imaging techniques for detection and management of endoleaks after endovascular aortic aneurysm repair. Radiology. 2007; 243 (3): 641-55; Hong C, Heiken J P, Sicard G A et-al. Clinical significance of endoleak detected on follow-up CT after endovascular repair of abdominal aortic aneurysm. AJR Am J Roentgenol. 2008; 191 (3): 808-13; Bashir M R, Ferral H, Jacobs C et-al. Endoleaks after endovascular abdominal aortic aneurysm repair: management strategies according to CT findings. AJR Am J Roentgenol. 2009; 192 (4): W178-86; and Rozenblit A M, Patlas M, Rosenbaum A T et-al. Detection of endoleaks after endovascular repair of abdominal aortic aneurysm: value of unenhanced and delayed helical CT acquisitions. Radiology. 2003: 227 (2): 426-33.

SUMMARY OF THE INVENTION

The present invention provides methods, materials, apparatus, and systems for the fabrication of covered stents, also referred to as grafts, used for a variety of intravascular and other intraluminal purposes. A particular use will be in Thoracic Endovascular Aortic Repair (TEVAR) procedures where the covered stents line the interior of an aortic aneurysm to inhibit further dilation and prevent rupture. The covered stents of the present invention will have a porous cover layer which promotes tissue-ingrowth and "merging" of the material with the native wall. In vivo implantation of the covered stents may be performed using a minimally invasive approach by crimping the device and delivering the devise intravascularly and/or transcutaneously to the site of implantation. The covered stents will have a particularly high recovery which will help prevent endovascular leaks after implantation. Another particular use will be as the base or anchor component of a prosthetic heart or other valve where high recovery will help assure proper seating of the valve in the native annulus while minimizing leakage around the valve.

The present invention can also provide a docking station or tubular body that acts as an adapter rather than just a support structure and will be configurable to provide more complex shapes in addition to straight tubes as in U.S. Pat. No. 7,922,761, described above. The tubular supports of the present invention will be particularly useful to provide or be docked with prosthetic valves where the tubular support serves as an outer support which is attached to or integrated with valve leaflets which may be formed at last partly from the same materials as the docking station or scaffold. Preferred materials for the tubular support include electrospun, porous polymers that can be formed into scaffolds to provide the support and can also be molded or otherwise formed to provide the valve leaflets. The electrospun or other porous encapsulating materials are preferably resorbable, absorbable, or degradable materials which allow for cell and tissue integration to aid prevention, reduction or elimination of endoleakage.

In a first aspect, the present invention provides a method for electrospinning comprising medical articles, such as implantable prostheses. The methods use an electrospinning apparatus including a target and an applicator in fluid communication with a flowable polymer, typically a polymer carried in a solvent but alternatively a melted polymer. The applicator is configured to direct a stream of the polymer to the target. A first electromotive force is applied on the applicator and a second electromotive force is applied on the target to generate a first electrical potential therebetween. The polymer is delivered through the applicator onto the target to produce a first set of fibers while applying the first electrical potential to produce a first set of fibers having a first flowability, i.e. ability of the polymer solution to flow to the target. In particular, the flowable polymer is delivered through the applicator onto the target under first delivery conditions that provide a first flowability while applying the first electrical potential to produce an inner layer comprising the first set of fibers. The delivery conditions are then adjusted to provide a second flowability to produce a second set of fibers to provide an adhesive layer between the inner layer and on outer layer, as will be described below. The second flowability will generally be greater than that of the first flowability, i.e. the conditions will be adjusted so that the second polymer solution that material reaches the target in a "semi-wet" state, i.e. it still contains solvent and therefore is adhesive to the polymer layer that is already formed on the target. The flowability should however not be increased so much that the material reaches the target with a wetness that would result in residual solvent and material soaking through the inner layer, potentially dissolving inner layer as well as creating an undifferentiated polymer mass.

The delivery conditions may be adjusted in a number of ways. In a first embodiment, the electrical potential between the applicator and the target may be changed to adjust the flowability of the fiber solution. For example, at least one of the first and second electromotive forces on the applicator and the target may be changed to generate a second electrical potential therebetween. Alternatively, a separation distance between the applicator and the target may be changed and as a result of a change in electrical field, the jet will not whip. In other embodiments, the flowability may be adjusted by delivering a mixture of at least first and second flowable polymers and adjusting the relative amounts of each flowable polymer to change the flowability of the mixture. For example, the at least first and second polymers may be delivered from at least first and second nozzles, and the relative amounts of each being delivered through each nozzle be adjusted to change the combined flowability. Similarly, two different solutions may be used with one being specifically tailored not to whip.

Still other approaches include using a focusing ring to accelerate jet and hinder whipping where the focusing ring is positively charged which elongates the straight region of the jet. The focusing ring can be switched off after wet spinning. The solution flow rate can be altered to selectively force a whipping or straight jet formation. Larger nozzle diameters might be employed to achieve a linear jet. By suturing the environment with solvent, drying of the fibers would be inhibited, and use of gas sheath would reduce whipping due to high solvent amount on fibers surface.

The polymer having an adjusted flowability (flowability) continues to be delivered through the applicator onto the target while applying the second electrical potential to produce a second set of fibers having a second flowability. The polymer is typically delivered in a solvent and the flowability correlates with a solvent fraction. Alternatively, the polymer may be delivered by melt-electrospinning. Melt electrospinning does not use solvents but heats the polymer to cause it to melt to become flowable, where the resulting molten polymer is delivered through the applicator onto the target while applying an electrical potential to produce the bonding between successive layers deposited via solution electrospinning and/or melt electrospinning. The flowability of a polymer delivered by melt electrospinning can be adjusted be adjusting the temperature.

Usually, at least one of the first and second electromotive forces is changed so that the second set of fibers has a higher solvent fraction than the first set of fibers so that the second set of fibers can act as an adhesive layer to a third or outer set of fibers applied over the second set of fibers. Typically, at least one of the first and second electromotive forces on the applicator and the target is further changed to generate a third electrical potential therebetween. The third layer is then formed by continuing to deliver the solution through the applicator onto the target to while applying the third electrical potential to produce a third set of fibers having a third solvent fraction over the second set of fibers, wherein the second set of fibers acts as an adhesive between the first and third sets of fibers.

In other embodiments, the second set of fibers may comprise an amount of the first solvent sufficient to confer flow properties on fibers; the second set of fibers may have a substantially flattened cross section; the second set of fibers may be ribbon-like; the second set of fibers may have a more flattened cross section on average than the first set of fibers; the first and second electromotive forces may be selected to provide a potential difference in the range between 1 kV and 150, typically in the range from 1 kV to 30 kV. The first electromotive force typically contributes from 50% to 100% of the potential difference and the second electromotive force typically contributes from 0% to 50% of the potential difference.

In preferred embodiments, the methods of the present invention may further comprise applying a release agent on the target before delivering the first solution. The release agent may comprise an organic phase such as ethanol or other solvent that does not dissolve the polymer. Alternatively, the release agent may comprise polyethylene glycol or polyethylene oxide. The release agent may be applied to the target in any conventional manner such as spraying, dipping, painting, or electrospinning, preferably being applied by electrospinning using the same apparatus and setup used for electrospinning the layers of the device, typically with a fourth potential difference between the applicator where the release agent solution is applied through the applicator onto the target to apply the release agent while applying the fourth potential difference. Optionally, the first set of fibers, may be rinsed with a release agent solvent that at least partially dissolves the release agent to allow the first set of fibers to be removed from the target. The release agent solvent will usually but not necessarily be an aqueous solution.

Optionally, the target may be rinsed with a second release agent solvent after electrospinning to produce the first set of fibers, wherein the second solvent at least partially dissolves the coating to release the first set of fibers. The solvent used does not dissolve the polymer constituting the first set of fibers. The target may comprise a variety of electrically conductive materials that can be formed into a desired geometry, such as aluminum, stainless steel, copper, chromium, and the like.

In a second aspect of the present invention, an endoprosthesis may be covered, laminated or encapsulated using an electrospinning apparatus comprising a target configured to removably receive the endoluminal prosthesis over an exterior surface thereof, an applicator configured to direct a stream of a solution comprising a polymer and a solvent to the target, and an energy source electrically coupled between the applicator and the target. The energy source is used to apply an electric potential between the applicator and the target, and a first solution is delivered through the applicator onto the target while applying the electric potential to form an inner layer comprising a first set of fibers. The endoluminal prosthesis is positioned at least partially around the inner layer to overlie the first set of fibers, and a third solution is delivered over the endoluminal prosthesis and the inner layer while applying an electric potential to produce an outer layer comprising a third set of fibers. The inner and outer layers, corresponding the first and third sets of fibers respectively, are adhered to each other (preferably by the adhesive layer produced by applying the second set of fibers) and to the endoluminal prosthesis to laminate the endoluminal prosthesis therebetween, and the endoluminal prosthesis is annealed and dried. After drying, the endoluminal prosthesis is removed from the target.

Optionally, the outer layer may be formed over only a portion if the inner layer and/or an endoprosthesis encapsulated between the inner and outer layers. For example, The outer layer can be configured to be compatible with the placement of leaf elements on a prosthetic heart valve being fabricated by the methods described herein. Straight e-spinning of the fibers of the outer layer can optionally be used to better control the area of deposition. Further optionally, masking using aluminum foil or other materials can be used to control the area of deposition.

In other embodiments, an adhesive layer may be formed between the inner and outer layers by delivering a second solution over the endoluminal prosthesis between steps (d) and (e) while applying an electrical potential to produce a second set of fibers (the adhesive layer described above) between the inner and outer layers formed by the first and the third sets of fibers, respectively. The electrical potential between the target and the applicator is adjusted to produce a higher solvent fraction in the second set of fibers that allows the second set of fibers to act as an adhesive between the first and the third sets of fibers.

A release agent may be applied over the target before delivering the first solution, where the release agent may comprise polyethylene-glycol or polyethylene and may be applied by spraying, dipping, painting, or electrospinning, typically by delivering a solution of the release agent through the applicator with a potential difference between the applicator and the target selected to electrospin the release agent onto the target prior to delivering the first solution These methods for covering or encapsulating an endoprosthesis may further comprise rinsing the inner layer with a solvent that at least partially dissolves the release agent to allow the first set of fibers to be removed from the target. The inner layer comprising the first set of fibers will usually be annealed, rinsed with the solvent, removed from the target, dried, and stored prior to replacing over a target and delivering the third set of fibers to form the outer layer, typically over the endoprosthesis. The encapsulated luminal endoprosthesis may be annealed, rinsed with solvent (if a release agent was used), removed from the target, dried, and stored after fabrication is complete.

BRIEF DESCRIPTION OF THE DRAWINGS

FIG. 1c is a graph showing the outer diameter (OD) of a tested covered stent during crimping and recovery.

FIGS. 2a-2q are photographs of the tested covered stent during crimping and recovery.

DETAILED DESCRIPTION OF THE INVENTION

Figure 1A:
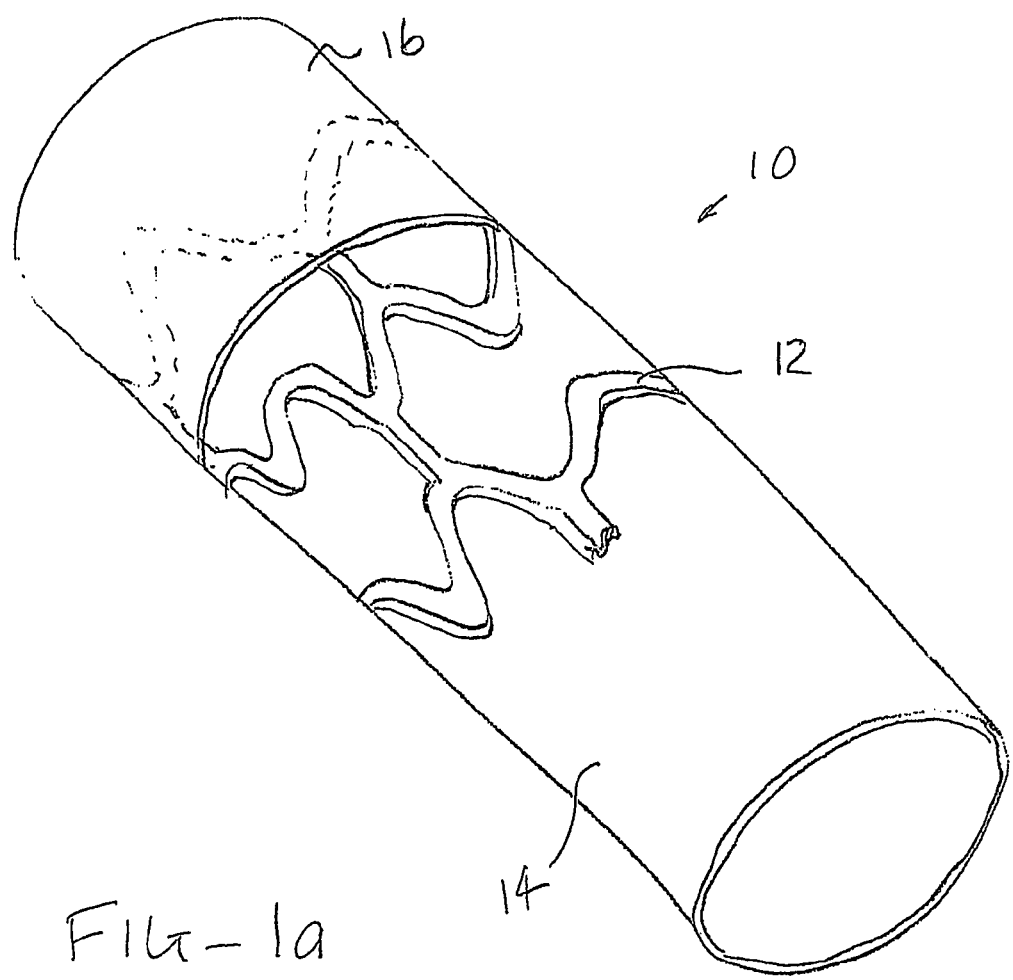
FIG. 1a illustrates an endoluminal prosthesis constructed in accordance with the principles of the present invention.

FIG. 1a illustrates a highly crimpable device 10 according to the present invention which includes a supporting stent 12 "sandwiched" or laminated between an inner electrospun layer 14 and an outer electrospun layer 16, preferably formed from a biodegradable polymer, such as PTFE, which are fused or bonded together during fabrication as described in detail below. The inner layer 14 may include integrated semi-lunar leaflets (not illustrated) providing a one-way valve for a prosthetic valve structure. Alternatively, the inner and outer layers of the device may both be generally tubular structures, where the inner layer could serve as a landing zone for a transcatheter (pulmonary) heart valve, which will be deployed in the same or in a separate procedure. Such tubular structures will also find use as grafts for treating aneurysms. Such structures may also find use whenever covered grafts are used in medical procedures.

Figure 1B:
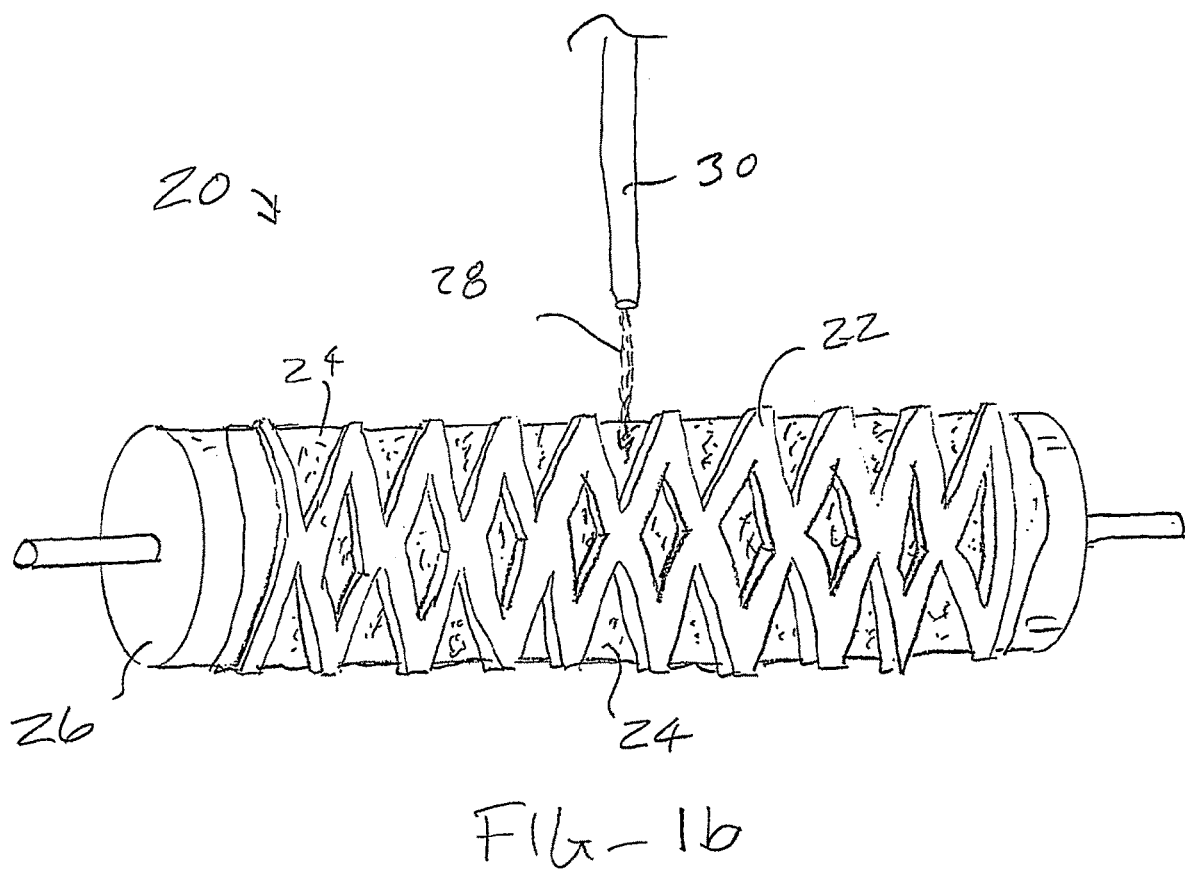
FIG. 1b illustrates electrospinning of the second and third sets of fibers over the first set of fibers after a stent has been placed over the first set of fibers.

FIG. 1b illustrates a system 20 for electrospinning the second and third sets of fibers over a stent 22 placed on a first set of fibers 24 that has been pre-formed into an inner layer over a mandrel 26. The outer part of the stent 22 is directly in the line of polymer spinning jet 28 directed from nozzle 30. As the "wet" second set of fibers is applied to the outwardly directed surfaces of the stent 22 and the inner layer 24, there will be some diffusion of the deposited wet fibers to the inside surface of the stent (between the stent and the inner layer) to reinforce the connection and bonding. However, after the wet spinning is completed and the normal spinning started (to form the outer skirt), further bonding is formed through the connection of the inner layer to the outer layer via the wet adhesive or glue layer.

The stents may have any conventional scaffold structure of the type used in medical procedures. The scaffolds may be formed from malleable materials, such as stainless steel, in order to be balloon expandable. Alternatively, the scaffolds may be formed from elastic materials, such as nickel-titanium alloy, in order to be self-expanding. Particular constructions for both balloon-expandable and self-expanding stents are well known and described in the patent and technical literature.

By controlling electrospinning and other fabrication conditions, porosity of the outer layer can be controlled to promote cellular in-growth to seal off paravalvular leakage and endovascular leakage. A high porosity of the outer layer or "skirt" also allows the skirt to be relatively thick skirt without compromising valve crimpability.

The electrospun layers of the present invention preferably comprise supramolecular polymers. Supramolecular polymers are formed when hydrogen bonding units are applied as associating end-groups of bi-functional molecules. The association constants must be sufficiently high to get a high degree of polymerization, which results in real polymer properties. Using supramolecular building blocks that assemble non-covalently via specific interactions, makes it possible to produce materials without tedious synthetic procedures but simply by assembly. In this way, it becomes easy to vary the amount and nature of the bioactive molecules and the nature of the polymers. This supramolecular approach bridges the gap between covalent modification and simple mixing of molecules and polymers. The first method leads to highly stable structures that lack dynamics. The latter, in contrast, results in very dynamic structures that lack stability. Using a supramolecular approach it is possible to control both stability and dynamics. A particular bioactive supramolecular system that we have previously described is based on oligocaprolactone end-functionalized with 2-ureido-4[1H]-pyrimidinone (UPy) groups. These UPy-moieties strongly dimerize via quadruple hydrogen bonding and display high association constants (Ka ¼ 106-107 L mol_l) in organic solvents. The UPy-functionalized oligocaprolactone shows much better mechanical properties than its unfunctionalized variation. These supramolecular polymer systems find already many uses in polymer applications.

EXAMPLES

Materials and Methods. Pictures were taken from the stent, before, during and after the experiment. Visual inspection was performed at all steps and written down in the study plan. In the study plan it was determined to crimp the stent to 12 mm, 10 mm, 8 mm, 6 mm, 5 mm and maximum possible for 5 minutes at each step. Because it was observed that it was most likely not possible to crimp the stent beyond 5 mm, an extra step of 7 mm was added. The outer diameter (OD) of the stent was measured and written down in the study plan, before crimping, directly after and 5 minutes after each crimping step. After crimping the stent to the maximum step of 5 mm, the stent was put into PBS. Pictures were made and the OD was measured at t=0, 5, 10, 15, 20 and 60 minutes. The ID of the sample that was tested was 30.30.080 T2.

The stents were prepared as follows. A first electrospinning solution was spun over a 29 mm cylindrical target, rotating at 100 RPM, to form the inner layer of the covered stent. The solution was an oligocaprolactone-based supramolecular polymer having a 23% polymer concentration and a polymer to solvent (chloroform, hexafluoroisopropanol, and methanol) ratio of 60/40/3. The covered stents were fabricated in a controlled environment of 23° C. and 35% relative humidity. After fabrication, the inner layer was removed by soaking it in water (~37° C.) and using a spatula to physically separate the layer from the metal target. The inner layer was dried at 37° C. and under vacuum. The inner layer and the stent were then mounted on a rotating mandrel and aluminum foil was used as a spacer to ensure that the inner layer and the mandrel had good contact. Additional oligocaprolactone-based supramolecular polymer (23% dissolved in chloroform, hexafluoroisopropanol, and methanol –60/40/3) was electrospun at 9 kV (5 kV, –4 kV) to fabricate the glue/adhesive layer. After applying the glue/adhesive layer, the same solution was electrospun for 20 minutes at 8 kV (7 kV, –1 kV) to create the outer layer of the stent.

Results. The direct recovery of the stent was above 90% for crimping down to 8 mm. After 5 minutes the OD recovery is above 90% for all the crimping steps. This is shown in FIG. 1c. Changes to the covered stent as it is crimped and recovered are shown in FIGS. 2a-2q. Visual inspection showed minimal damage to the covered stent for all the crimping steps. Only after the maximum crimping step, two tiny holes appeared in the scaffold (one hole visible in FIG. 2n). The creases in the material become deeper when crimping to a smaller diameter. After putting the stent in pre-heated PBS (37° C.), the creases start fading immediately until they are almost gone after 1 hour. Minimal damage of the 30 mm covered stent was observed after 6 crimping steps, with a maximum crimping step of 5 mm. The observed damage was caused by friction between the scaffold and the crimping device. The diameter was able to recover to 96% of the original diameter within 5 minutes after the maximum crimping step. Therefore it can be concluded that the 30 mm covered stent can be crimped to an OD of 5 mm with full recovery and minimal permanent damage.

The foregoing examples are not intended to limit the scope of the invention. All modifications, equivalents and alternatives are within the scope of the invention.

What is claimed is:

1. A method for electrospinning comprising:
    (a) providing an electrospinning apparatus comprising:
        (i) a target,
        (ii) an applicator in fluid communication with a flowable polymer, said applicator configured to direct a stream of the flowable polymer to the target,
    (b) applying a first electromotive force on the applicator and a second electromotive force on the target to generate a first electrical potential therebetween;
    (c) delivering the flowable polymer through the applicator onto the target under first delivery conditions that provide a first flowability while applying a first electrical potential to produce a first set of fibers;
    (d) adjusting the delivery conditions to provide a second flowability; and
    (e) delivering the flowable polymer through the applicator onto the target to while after adjusting the delivery conditions while applying an electrical potential to produce a second set of fibers, wherein the method further comprises applying a release agent on the target before delivering the first flowable polymer and wherein the method further comprises rinsing the first set of fibers with a release agent solvent that at least partially dissolves the release agent to allow the first set of fibers to be removed from the target.

2. The method of claim 1, wherein adjusting the delivery conditions comprises changing at least one of the first and second electromotive forces on the applicator and the target to generate a second electrical potential therebetween.

3. The method of claim 1, wherein adjusting the delivery conditions comprises changing a separation distance between the applicator and the target to generate a second electrical potential therebetween.

4. The method of claim 1, wherein adjusting the delivery conditions comprises delivering a mixture of at least first and second flowable polymers and adjusting the relative amounts of each flowable polymer to change the flowability of the mixture.

5. The method of claim 4, wherein delivering the mixture of at least first and second flowable polymers and adjusting the relative amounts of each flowable polymer comprises delivering the at least first and second polymers from at least first and second nozzles and adjusting the amounts being delivered through each nozzle.

6. The method of claim 1, wherein the flowable polymer comprises a polymer in a solvent solution and wherein the first set of fibers has a first solvent fraction and the second set of fibers has a second solvent fraction.

7. The method of claim 6 wherein the second set of fibers has a higher solvent fraction than the first set of fibers so that the second set of fibers can act as an adhesive to a third set of fibers when applied over the second set of fibers.

8. The method of claim 7 further comprising:
(f) changing at least one of the first and second electromotive forces on the applicator and the target to generate a third electrical potential therebetween; and
(g) continuing to deliver the solution through the applicator onto the target to while applying the third electrical potential to produce a third set of fibers having a third solvent fraction over the second set of fibers, wherein the second set of fibers acts as an adhesive between the first and third sets of fibers.

9. The method of claim 7 wherein said second set of fibers comprises an amount of the first solvent sufficient to confer flow properties on fibers.

10. The method of claim 1 wherein said second set of fibers have a substantially flattened cross section.

11. The method of claim 1 wherein said second set of fibers have a more flattened cross section on average than the first set of fibers.

12. The method of claim 1 wherein the first and second electromotive forces are selected to provide a potential difference in the range between 1 kV and 150 kV.

13. The method of claim 12 wherein the first electromotive force contributes from 50% to 100% of the potential difference and the second electromotive force contributes from 0% to 50% of the potential difference.

14. A method as in claim 1, wherein the release agent comprises ethanol.

15. A method as in claim 1, wherein the release agent comprises polyethylene-glycol or polyethylene oxide.

16. A method as in claim 1, wherein the release agent is applied by spraying, dipping, painting, or electrospinning.

17. The method of claim 16, wherein the release agent is applied by electrospinning with a fourth potential difference between the applicator and the target and delivering the solution through the applicator onto the target to apply the release agent while applying the fourth potential difference.

18. The method of claim 1 wherein the release agent solvent is aqueous.

19. The method of claim 1 further comprising rinsing the target with a further solvent after electrospinning to produce the first set of fibers in order to remove the first set of fibers, wherein the further solvent at least partially dissolves the layer containing the release agent.

20. The method of claim 19 wherein the further solvent does not dissolve the polymer.

21. The method of claim 1 wherein the target comprises a material selected from the group consisting of aluminum, stainless steel, copper, and chromium.

22. A method for covering a medical prosthesis comprising:
(a) providing an electrospinning apparatus comprising:
(i) a target configured to removably receive the medical prosthesis over an exterior surface thereof,
(ii) an applicator configured to direct a flowable polymer to the target, and
(iii) an energy source electrically coupled between the applicator and the target;
(b) applying an electric potential with the energy source between the applicator and the target;
(c) delivering a first amount of the flowable polymer through the applicator onto the target while applying the electric potential to form an inner layer comprising a first set of fibers;
(d) positioning the medical prosthesis at least partially around the inner layer to overlie the first set of fibers;
(e) delivering a third amount of a flowable polymer over the medical prosthesis and the inner layer while applying the electric potential to produce an outer layer comprising a third set of fibers to form an outer layer, wherein the flowable polymer comprises a polymer in a solvent solution and wherein the first set of fibers has a first solvent fraction and the third set of fibers has a third solvent fraction;
(f) adhering the first and third sets of fibers to each other and the medical prosthesis by delivering a second set of fibers of the polymer in a solvent over the medical prosthesis between the steps (d) and (e) while applying the electric potential to produce an adhesive layer comprising a second set of fibers between the first and the third sets of fibers, wherein the flowability of the second set of fibers is adjusted to allow the second set of fibers to act as an adhesive between the first and the third sets of fibers, and wherein said second set of fibers have a substantially flattened cross section, wherein the substantially flattened cross section of the second set of fibers is on average more than for the first set of fibers;
(g) annealing and drying the medical prosthesis; and
(h) removing the annealed and dried medical prosthesis from the target.

23. The method of claim 22 further comprising applying a release agent on the target before delivering the first solution.

24. The method of claim 23 wherein said release agent comprises polyethylene-glycol or polyethylene oxide.

25. The method of claim 24 wherein said release agent is applied by spraying, dipping, painting, or electrospinning.

26. The method of claim 25, wherein the release agent is applied by delivering a solution of the release agent through the applicator with a potential difference between the applicator and the target selected to electrospin the release agent onto the target prior to delivering the first solution.

27. The method of claim 22 further comprising rinsing the first set of fibers, with a release agent solvent that at least partially dissolves the release agent to allow the first set of fibers to be removed from the target.

28. The method of claim 27, wherein the inner layer comprising the first set of fibers is annealed, rinsed with the release agent, removed from the target, dried, and stored prior to replacing over a target and delivering the second solution to form the outer layer.

29. The method of claim 28, wherein the inner layer comprising the first set of fibers is annealed, rinsed with the release agent, removed from the target, dried, and stored prior to replacing over a target and delivering the second solution to form the outer layer comprising the second set of fibers.

30. The method of claim 22, wherein the luminal prosthesis comprising the first set of fibers and the third set of fibers is annealed, rinsed with release agent, removed from the target, dried, and stored after fabrication is complete.

31. The method of claim 22, wherein the luminal prosthesis comprising the first set of fibers and the third set of fibers is annealed, rinsed with release agent, removed from the target, dried, and stored after fabrication is complete.

32. The method of claim 22, wherein adjusting the delivery conditions comprises changing at least one of the first and second electromotive forces on the applicator and the target to generate a second electrical potential therebetween.

33. The method of claim 22, wherein adjusting the delivery conditions comprises changing a separation distance between the applicator and the target to generate a second electrical potential therebetween.

34. The method of claim 22, wherein adjusting the delivery conditions comprises delivering a mixture of at least first and second flowable polymers and adjusting the relative amounts of each flowable polymer to change the flowability of the mixture.

35. The method of claim 34, wherein delivering the mixture of at least first and second flowable polymers and adjusting the relative amounts of each flowable polymer comprises delivering the at least first and second polymers from at least first and second nozzles and adjusting the amounts being delivered through each nozzle.

36. The method of claim 22, wherein the medical prosthesis is an endoluminal prosthesis or a vascular graft.

* * * * *